US00RE50687E

(19) United States
(12) Reissued Patent
Tegen et al.

(10) Patent Number: US RE50,687 E
(45) Date of Reissued Patent: Dec. 9, 2025

(54) SYSTEMS, DEVICES, AND/OR METHODS FOR MANAGING HEALTH

(71) Applicant: A.R.M.S Defense, Inc., Mooreville, NC (US)

(72) Inventors: Spencer Mckay Tegen, Blanding, UT (US); Adam Moroni Shumway, Mooresville, NC (US)

(73) Assignee: A.R.M.S. Defense Inc., Monticello, UT (US)

(21) Appl. No.: 18/466,776

(22) Filed: Sep. 13, 2023

Related U.S. Patent Documents

Reissue of:
(64) Patent No.: 11,116,413
Issued: Sep. 14, 2021
Appl. No.: 16/428,489
Filed: May 31, 2019

U.S. Applications:
(60) Provisional application No. 62/764,381, filed on Aug. 2, 2018.

(51) Int. Cl.

| | |
|---|---|
| ***A61B 5/024*** | (2006.01) |
| ***A61B 5/00*** | (2006.01) |
| ***A61B 5/0205*** | (2006.01) |
| ***A61B 5/11*** | (2006.01) |
| ***G08B 25/01*** | (2006.01) |
| ***G16H 40/67*** | (2018.01) |

(52) U.S. Cl.
CPC ..... *A61B 5/02438* (2013.01); *A61B 5/0205* (2013.01); *A61B 5/1112* (2013.01); *A61B 5/681* (2013.01); *A61B 5/746* (2013.01); *A61B 5/747* (2013.01); *G08B 25/016* (2013.01); *A61B 5/0006* (2013.01); *A61B 5/0022* (2013.01); *A61B 5/1118* (2013.01); *A61B 5/6824* (2013.01); *A61B 5/6829* (2013.01); *A61B 2562/0219* (2013.01); *G16H 40/67* (2018.01)

(58) Field of Classification Search
CPC . A61B 5/02438; A61B 5/0205; A61B 5/1112; A61B 5/681; A61B 5/746; A61B 5/747; A61B 5/0006; A61B 5/0022; A61B 5/1118; A61B 5/6824; A61B 5/6829; A61B 2562/0219; G06B 25/16; G16H 40/67
See application file for complete search history.

(56) References Cited

U.S. PATENT DOCUMENTS

| | | | | |
|---|---|---|---|---|
| 9,922,537 | B2 * | 3/2018 | Shah | F41H 13/0018 |
| 10,154,460 | B1 * | 12/2018 | Miller | A61B 5/1455 |
| 10,299,102 | B1 * | 5/2019 | Suxena | H04W 4/90 |
| 2008/0001764 | A1 * | 1/2008 | Douglas | G07C 9/28 340/539.11 |
| 2008/0088437 | A1 * | 4/2008 | Aninye | H04W 4/18 455/456.6 |
| 2010/0231378 | A1 * | 9/2010 | Ward | A61B 5/318 340/539.11 |

(Continued)

*Primary Examiner* — Robert L Nasser
(74) *Attorney, Agent, or Firm* — IPTechLaw

(57) ABSTRACT

Certain exemplary embodiments can provide a device that comprises a heart monitor. The device can further comprise GPS hardware and machine instructions. The device comprises a wireless transceiver and a battery. The battery that provides electrical energy to the wireless transceiver and a processor. The processor is constructed to receive signals from the heart monitor and determine that an emergency has occurred.

20 Claims, 9 Drawing Sheets

(56) References Cited

U.S. PATENT DOCUMENTS

| | | | | |
|---|---|---|---|---|
| 2010/0267361 | A1* | 10/2010 | Sullivan | G01S 19/17 455/404.2 |
| 2013/0179540 | A1* | 7/2013 | Isozu | H04L 67/02 709/218 |
| 2013/0217332 | A1* | 8/2013 | Altman | G06Q 20/3224 455/3.01 |
| 2015/0031325 | A1* | 1/2015 | Huh | H04W 4/027 455/404.2 |
| 2016/0066189 | A1* | 3/2016 | Mahaffey | H04M 15/7652 455/405 |
| 2017/0223494 | A1* | 8/2017 | Xie | H04W 12/126 |
| 2017/0352194 | A1* | 12/2017 | Sculli | G06T 9/00 |
| 2017/0357969 | A1* | 12/2017 | Huang | G06F 21/316 |
| 2019/0369569 | A1* | 12/2019 | Olsen | G06K 7/1095 |

* cited by examiner

SYSTEMS, DEVICES, AND/OR METHODS FOR MANAGING HEALTH

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCES TO RELATED APPLICATIONS

This application claims priority to, and incorporates by reference herein in its entirety, U.S. Provisional Patent Application Ser. No. 62/764,381, filed Aug. 13, 2018.

BRIEF DESCRIPTIONS OF THE DRAWINGS

A wide variety of potential practical and useful embodiments will be more readily understood through the following detailed description of certain exemplary embodiments, with reference to the accompanying exemplary drawings in which.

DETAILED DESCRIPTION

Figure 1:
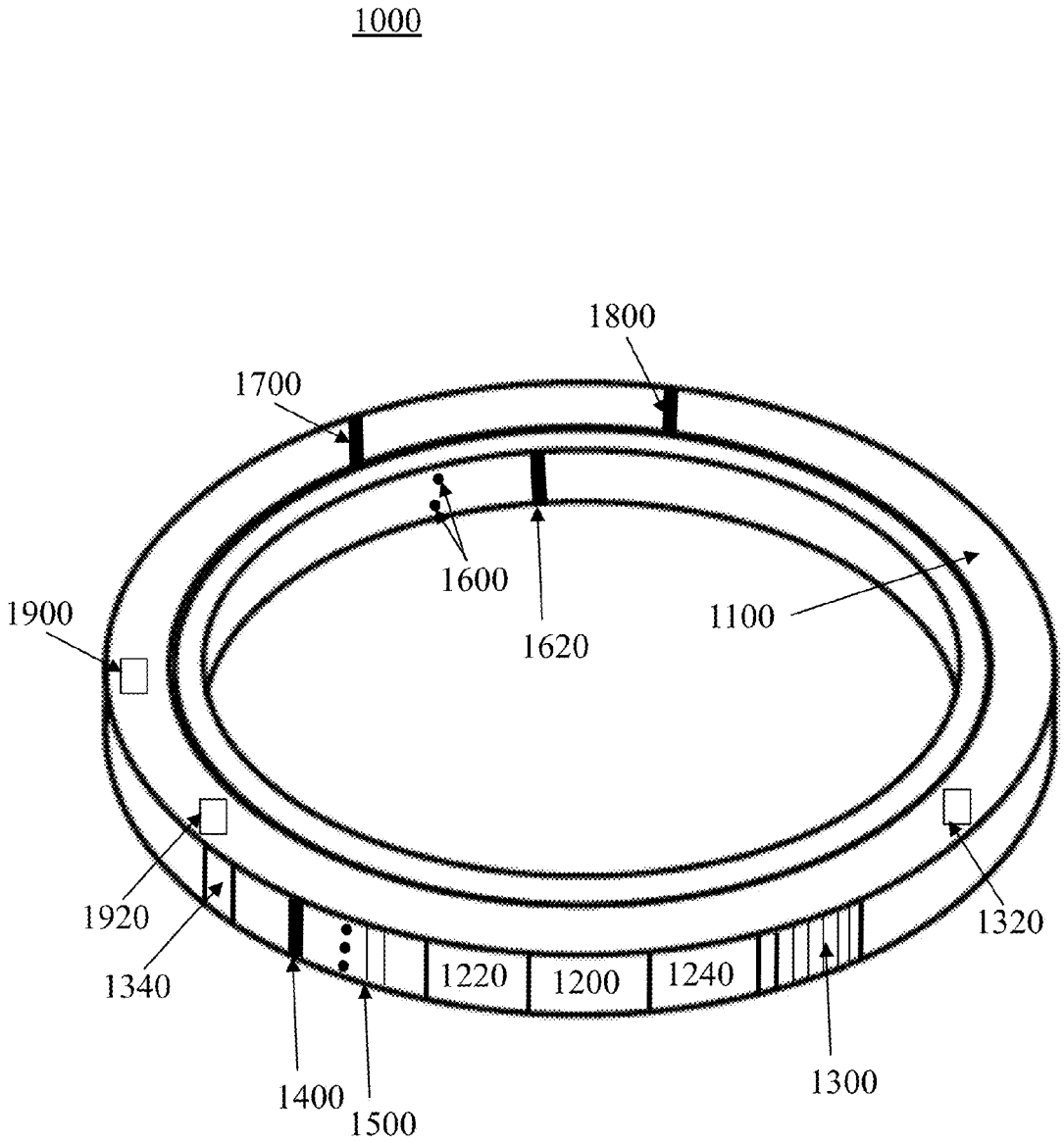
FIG. 1 is a perspective view of an exemplary embodiment of a device 1000.

Certain exemplary embodiments can provide a device that comprises a heart monitor. The heart monitor can, for example, monitor heart rate and/or electrocardiogram information, etc. The device can further comprise GPS hardware and machine instructions. The device comprises a wireless transceiver and a battery. The battery provides electrical energy to the wireless transceiver and a processor. The processor is constructed to receive signals from the heart rate monitor and determine that an emergency has occurred.

Certain exemplary safety response services or systems on the market require human interaction in order for the system to work. A problem with the present state of the industry is that there are a lot of circumstances where pushing a button or working a smart device isn't workable for a wearer of smart devices. According to the FBI approximately 600,000-900,000 Americans disappear every year; almost 70% of which are under the age of 21. Annual crime statistics in the United States show approximately 15,000-20,000 murders a year, approximately 90,000-100,000 rapes, and approximately 1.2 million violent crimes according to an FBI database. None of the current systems on the market are set up to reduce chances of any such disappearances without a user pushing one or more buttons or otherwise interacting and/or managing a smart device.

Certain exemplary embodiments are constructed to automatically locate an individual utilizing GPS location technology.

Certain exemplary embodiments provide a personal safety automatic response system.

Certain exemplary embodiments can eliminate any need to push a button or work a smart device in order to alert friends, family, emergency medical technicians, police, fire fighters, response center, and/or any other first responders in the event of being attacked, raped, kidnapped, and/or killed. Each such event will trigger a response from the device, which will send time location and active GPS tracking. Another key feature to the device includes an alert being sent to any other individual who would like to be notified of alerts within a specific GPS range.

This will allow good Samaritans, police, community watch personnel, firefighters, EMTs, and/or others to be a witness or be able to intervene when an alert is triggered.

The device can be worn on a person's wrist or ankle and monitor their heart rate frequency (i.e., pulse) and/or electrocardiogram information of the person. If an individual pulse stops, dips, or spikes (fight or flight) the device will send an alert to one or more of the following, parents or guardians, family, neighborhood watch personnel, police, firefighters, EMT's, school teachers, security guards, emergency medical systems, and/or any other people that have subscribed to receive alerts in a predetermined geographical range. If the device travels outside a predetermined range (e.g., home, school, city, state, etc.) the device can be configured to trigger and send an alert. If the device is tampered with or an attempt is made to remove the device, an alert will be sent with a last known GPS location. If an individual is being raped or sexually assaulted, their heart rate will go out of normal rhythm by spiking or dropping (possibly due to being drugged and/or attacked) an alert will be sent out, and will activate a speaker for communication with a trusted contact or call center. With the GPS a user will have an ability to ping the device of an individual, even if no emergency is apparent, to locate someone who may have wondered off, gotten lost, or whose location is unknown. When a device or devices are purchased the owner can download a supporting app to a tablet, smart phone, smart watch or computer. Once installed the owner can be prompted to input information pertaining to a device wearer (e.g., age, height, weight, sex, ethnicity, eye color, and/or hair color, etc.) this information can be of value, for example, in a case of kidnapping.

When the alert goes out, the alert can comprise a description of the device holder so that those notified will know what to look for. If the device is removed, certain exemplary embodiments can still send an alert with information so that individuals will know what to look for.

The device can have one or more of the following features:

- a wireless transceiver, such as one constructed to utilize WiFi;
- a touch screen constructed to utilize a software application ("app").
- GPS location hardware and machine instructions;
- a speaker communicatively coupled to the wireless transceiver;
- a microphone;
- a rechargeable battery and/or a replaceable battery;
- a biometric sensor; and/or a band comprising a cable or other cut resistant material, the cut resistant material constructed to resist unauthorized removal of the band from the arm of a user.

Battery changes can be conditioned upon approval of an owner/operator of the device. The device can also be removed with permission of the device owner/operator. For example, the device can be unlocked with a key code, fingerprint, and/or voice recognition, etc. If the battery charge of the device drops below a predetermined threshold (e.g., 10% of power remaining), the device can send a warning and a GPS location prior to shutting down and can also go into lock mode. In certain exemplary embodiments the device cannot be unlocked via any of the prior mentioned unlock methods until sufficient power is restored to the device (e.g., the battery is recharged and/or replaced). The device can comprise sensors in the wristband that will trigger with remaining battery power if an attempt is made to remove the device. The information recorded by the device can be set to upload to a "cloud" back up service, laptop, desk top, tablet, smartphone and/or other devices. The information gathered concerns the wearer of the device. A person having been granted authority can be permitted to see and review wearer data in case of a minor. Information concerning a minor can be more restricted than information concerning adults until after the minor reaches the age of eighteen. Any information given or shared with via the device can be restricted in use to for the purposes of reporting detected emergencies and/or for making the heart monitor more accurate and/or making the system better capable of filtering out false responses.

If a signal is lost in an arca where cellular telephone service is good, a last known location will be sent in an alert until service is restored. If cell phone jammers are used to block the signal of the device, the last known signal can be sent to predetermined entities until service is restored.

The device can comprise:

a speaker;

a heart rate monitor;

a first screen constructed to display information related to the heart rate monitor;

a GPS system comprising a transceiver and processing unit;

one or more of multiple available colors to choose from;

a band, such as a coiled band, that is resistant to cutting; and/or a second screen, which may double as a smart watch with text and/or call notification capability; etc.

Certain exemplary embodiments can comprise:

a band;

a speaker;

a GPS system comprising a transceiver and processing unit; and/or a heart rate monitor, which can be specially designed for a child and/or elderly person; etc.

Children might not need a screen while at school and such embodiments without a screen can be selected for those that are not up to date in the technology world.

Scenarios of exemplary applications comprise:

Scenario 1

In an exemplary embodiment a mom and/or a dad obtain an exemplary safety product and perform one or more of the following:

Download product software (e.g., an "app") on an Android® (Android is a registered trademark of Google Inc. of Mountain View Calif.) device, Apple© (Apple is a registered trademark of Apple, Inc. of Cupertino, Calif.) device, personal computer, and/or tablet, etc.

Enter safety product purchaser/owner information (e.g., name, birthday, address, household members names and/or ages, etc.).

Enter safety product user/wearer information. For example, a child name (e.g, John Smith), age (e.g., six years old), height (e.g., 4' 2"), weight (e.g., 41pounds), eye color (e.g., blue), hair color (e.g., blonde), etc.

GPS perimeters can be set. For example, GPS perimeters can be set at:

1st perimeter 8:00 pm-7:30 am at a five block radius from home.

2nd perimeter 7:30 am-3:15 pm at a one block radius from school Monday-Friday and holidays, etc.

Set a security code (i.e., personal identification number) to remove and/or put on device. A device wristband can send an alarm (sent to specified devices or phone numbers) if removed or put on without entering the security code.

Enter contacts that will receive alerts. For example, a parent, a grandparent, a sibling, a system call center, and/or a friend, etc.

Fully charge device (e.g., for approximately 24 hours).

Charge device regularly (e.g., every night).

Set up a memory device to store all recorded information. All recorded information can be the property of the owner/user. A minor's personal information from device can comprise their own information as well as their legal guardian, each of which can have rights to view data until the minor reaches the age of 18 and/or can be deemed to have rights to view information withdrawn after the minor reaches the age of 18.

Wear the device and perform activities, for example, one or more of the following activities to get an expected heart rate range and/or electrocardiogram profile: exercise (e.g., run and jump), wear the device a couple of times while sleeping, to establish a base resting and sleeping heart rate.

Go for a walk, experience laughter, physical interaction that is safe and appropriate (e.g., being tickled, hugged, etc.), and/or any other activity to help the device learn the bounds of a user's normal heart rate perimeters.

For example, a parent can send the child out to walk to school (e.g., couple blocks away).

A child can get picked up on his way to school by a stranger with candy. An alarm might not be triggered from fight or flight. However, the child is transported out of a predetermined GPS range (e.g., two blocks outside of the range) and the parent is immediately alerted.

The parent can receive an alert that the child is not on course to school. The parent can follow the signal to find the child and/or notify law enforcement to intervene to recover the child from being abducted.

Scenario 2

Sara buys a safety tech device

Sara is a college student away from home.

Download product software (e.g., an "app") on an Android® (Android is a registered trademark of Google Inc. of Mountain View Calif.) device, Apple© (Apple is a registered trademark of Apple, Inc. of Cupertino, Calif.) device, personal computer, and/or tablet, etc.

Enter safety product purchaser/owner information (e.g., name, birthday, address, household members names and/or ages, etc.).

Enter safety product user/wearer information. For example, a child name (e.g, John Smith), age (e.g., 21 years old), height (e.g., 5' 5"), weight (e.g., 121 pounds), eye color (e.g., blue), hair color (e.g., blonde), etc.

GPS perimeters can be set. For example, GPS perimeters can be set at:

1st perimeter 8:00 pm-7:30 am at a five block radius from residence.

2nd perimeter 7:30 am-4:30 pm 20 mile from school Monday-Friday and holidays, etc.

Set a security code (i.e., personal identification number) to remove and/or put on device. A device wristband can send an alarm (sent to specified devices or phone numbers) if removed or put on without entering the security code.

Enter contacts to receive alerts. For example, roommates, friends, family members, a system call center, etc.

Fully charge device (e.g., for approximately 24 hours).

Charge device regularly (e.g., every night).

Set up a memory device to store all recorded information. All recorded information can be the property of the owner/user. A minor's personal information from device can comprise their own information as well as their legal guardian, each of which can have rights to view data until the minor reaches the age of 18and/or can be deemed to have rights to view information withdrawn after the minor reaches the age of 18.

Wear the device and perform activities, for example, one or more of the following activities to get an expected heart rate range and/or electrocardiogram profile: exercise (e.g., run and jump), wear the device a couple of times while sleeping, to establish a base resting and sleeping heart rate.

Go for a walk, experience laughter, physical interaction that is safe and appropriate (e.g., being tickled, hugged, etc.) and/or any other activity to help the device learn the bounds of a user's normal heart rate perimeters Sara: goes for a jog later at night about three blocks away from apartment and gets grabbed and is being raped.

Roommate #1: gets alert that Sara's heart rate has spiked and she is located three blocks away. The roommate runs to Sara's location while calling police. The roommate sees the attacker and is now an eyewitness.

Attacker: sees that someone is coming and sees him, the attacker runs away and is pursued by police.

Sara is a little shaken and bruised but otherwise okay.

Scenario #3

Tom buys a safety tech device.

Tom is also a student and is running a start up business.

Download product software (e.g., an "app") on an Android® (Android is a registered trademark of Google Inc. of Mountain View Calif.) device, Apple © (Apple is a registered trademark of Apple, Inc. of Cupertino, Calif.) device, personal computer, and/or tablet, etc.

Enter safety product purchaser/owner information (e.g., name, birthday, address, roommates, dormmates, call center, and/or friends, etc.).

Enter safety product user/wearer information. For example, a person named (e.g, Tom Smith), age (e.g., 26 years old), height (e.g., 5' 11"), weight (e.g., 181pounds), eye color (e.g., blue), hair color (e.g., blonde), etc.

GPS perimeters can be set. For example, GPS perimeters can be set at:

1st perimeter 8:00 pm-7:30 am at a five block radius from residence.

2nd perimeter 7:30 am-4:30 pm at a 20 mile radius from school and/or business Monday-Friday and holidays, etc.

Set a security code (i.e., personal identification number) to remove and/or put on device. A device wristband can send an alarm (sent to specified devices or phone numbers) if removed or put on without entering the security code.

Enter contacts to receive alerts. For example, roommates, friends, family members, and/or a system call center, etc.

Fully charge device (e.g., for approximately 24 hours).

Charge device regularly (e.g., every night).

Set up a memory device to store all recorded information. All recorded information can be the property of the owner/user. A minor's personal information from device can comprise their own information as well as their legal guardian, each of which can have rights to view data until the minor reaches the age of 8and/or can be deemed to have rights to view information withdrawn after the minor reaches the age of 18.

Wear the device and perform activities, for example, one or more of the following activities to get an expected heart rate range and/or electrocardiogram profile: exercise (e.g., run and jump), wear the device a couple of times while sleeping, to establish a base resting and sleeping heart rate.

Go for a walk, experience laughter, physical interaction that is safe and appropriate (e.g., being tickled, hugged, etc.) and/or any other activity to help the device learn the bounds of a user's normal heart rate perimeters.

Tom: start up business is successful and gets bought out by big company and he lets his three employees know he was bought out and he doesn't own company.

Employee #2 files charges of rape against Tom.

Tom is arrested and facing serious charges. Dates and time of alleged encounter are revealed. Tom uses his device history to show his GPS location and heart rate at time of alleged incident. Charges are dropped and Tom is released.

Scenario #4

A son or daughter buys a safety tech device for elderly parent.

The device is bought for son or daughter's elderly parent(s).

Download product software (e.g., an "app") on an Android® (Android is a registered trademark of Google Inc. of Mountain View Calif.) device, Apple © (Apple is a registered trademark of Apple, Inc. of Cupertino, Calif.) device, personal computer, and/or tablet, etc.

Enter safety product purchaser/owner information (e.g., name, birthday, address, roommates, assisted living staff, system call center, and/or friends, etc.).

Enter safety product user/wearer information. For example, a person named (e.g. Jane Smith), age (e.g., 85 years old), height (e.g., 5' 3"), weight (e.g., 151 pounds), eye color (e.g., blue), hair color (e.g., gray), etc.

GPS perimeters can be set. For example, GPS perimeters can be set at:

1st perimeter 8:00 pm-7:30 am at a five block radius from residence.

2nd perimeter 7:30 am-4:30 pm at a three mile radius from residence, which would be within distance of a bowling ally and/or hair salon, etc.

Set a security code (i.e., personal identification number) to remove and/or put on device. A device wristband can send an alarm (sent to specified devices or phone numbers) if removed or put on without entering the security code.

Enter contacts to receive alerts. For example, assisted living home staff, friends, family members, system call center etc.

Fully charge device (e.g., for approximately 24 hours).

Charge device regularly (e.g., every night).

Set up a memory device to store all recorded information. All recorded information can be the property of the owner/user or their guardian(s).

Wear the device and perform activities, for example, one or more of the following activities to get an expected heart rate range and/or electrocardiogram profile: exercise (e.g., run and jump), wear the device a couple of times while sleeping, to establish a base resting and sleeping heart rate.

Go for a walk, experience laughter, physical interaction that is safe and appropriate (e.g., being tickled, hugged, etc.) and/or any other activity to help the device learn the bounds of a user's normal heart rate perimeters.

Mom falls between bed and wall can't move her arms, and has a slightly elevated heart rate for a prolonged time.

A son or daughter is sent a soft alert of mild or out of normal heart rate for mom (since this device is automatic no one has to push a button to get help).

The son or daughter calls mom but the phone isn't answered. The son or daughter drives to mom's home and finds mom stuck and helps her, and then calls for medical help to make sure she is okay.

Scenario #5

A mother is getting her son ready for school one morning. Her husband has already gone to work and she is running late herself. She gives her ten-year-old son a kiss on the cheek and he heads out the door to catch his bus. Not giving it another thought, the mother goes about getting ready to start her day.

On her way to work she suddenly hears a voice coming from her phone. "Mrs. Smith, this is Carol from Automatic Response Modern Security™ ("ARMS") and we have just received a notification that your child may be in distress." Concerned, she pulls over to check her child's GPS coordinates, which she can access via a convenient app located on her smartphone. The operator might state, "Mrs. Smith, I'm going to stay on the line with you. The police have been called and are en route to your son's location. We tried to make contact with him but there was no response. I'm going to need you to answer a few questions for me."

The dispatcher then proceeds to ask if this was a scheduled detour and if her son was out playing today. The dispatcher states that ARMS™ was alerted because the child's HEART RATE became elevated. In addition, an alarm was sent to a dispatch center to send emergency personnel. Once this happens a trained dispatcher can try to make contact with the wearer of the device via a speaker and/or send emergency services personnel. The wearer and the dispatcher are then able to communicate instantly with each other. The GPS component lets authorities track the wearer of the device in real time.

The operator might state, "Mrs. Smith, police are with your son. His potential abductor heard my voice and was scared off. He left your son on the side of the road. There is no need to worry. He's safe. Is there anything more I can do to help you today?"

Scenario #6

Jane, a college student, was walking home one evening after class. It was a beautiful night and the street was well lit. There were no cars and the air was silent. She still felt a little uneasy. That's when she heard footsteps behind her. Softly at first but slowly picking up speed, Jane decided to pick up her pace as well, but the footsteps were starting to match her own and even getting faster.

Jane remembered to put on her ARMS™ security watch before she left for school that morning. With the touch of a button she is instantly connected to a dispatcher who is cager to help her.

The operator might state, "This is John with Automatic Response Modern Security. How may I help you today, Jane?" As a member of ARMS™, Jane's information, including: name, date of birth, gender, address, as well as current location, are all transmitted to the ARMS™ dispatch team.

"I'm being followed and I don't know who they are." Jane says in a panic.

The operator might state, "Just stay on the line with me and we'll make sure you stay safe. Police have been dispatched to your location."

Jane might say, "Thank you."

With GPS feature and the ability to make calls to and from the device, attacks can be prevented or quickly addressed. Exemplary features also make it possible for a dispatcher to give directions to help the wearer of the device navigate safely away from their attacker.

Scenario #7

The snow was fresh and the air was cold. Matthew was deep in the woods surrounding his town. For most of his life Matthew has been a trapper and knew the area better than most. As Matthew was driving down a snow-covered road, he suddenly realized his axle broke. The sun had long since set and he knew it would be difficult to survive the night. Being so far away from civilization there was no cell phone coverage available. Lucky for Matthew he was a member of ARMS™ and was wearing his device. With the easy one touch system he was able to call for help. Within an hour rescue crews were able to access the GPS feature located on his device and Matthew was returned home safe and sound.

Scenario #8

Early one morning a knock was heard at the door. Steve and Anne were going about their morning like usual. Their three children were upstairs getting ready. The family had decided to go for a hike. Steve answered the door to find an officer. The officer brought news that a fire had broken out in the nearby forest that surrounds their peaceful community. The fire department was unable to control the blaze and an evacuation order was sent out. The authorities were going from house to house to tell people to leave immediately.

Anne raced upstairs to find only two of their children. Panicked she called out their name while taking the others to join their father downstairs. One child was not in the house. Thankfully they had an ARMS™ alert device and each member of the family was given one.

While Anne watched the children Steve logged into the app and used the GPS locator to find their missing child. The heart monitoring feature showed they were a little excited. Quickly, Steve raced to the backyard to find the child staring at the fire, which was raging in the distance behind their house.

With all three children were taken to their vehicle. Steve and Anne gathered what they could and drove off to safety.

Certain exemplary embodiments can be used in many other situations and scenarios (e.g. nursing home for dementia patients that can wonder off, any organization that has representatives both foreign and domestic, military applications, etc.).

FIG. 1 is a perspective view of an exemplary embodiment of a device 1000, which can comprise:

a band 1100 comprising a cut resistant material, the cut resistant material constructed to resist unauthorized removal of the band from the arm of a user;

a pull band 1400;

a band adjustment 1500;

a first touch screen 1200 constructed to utilize a software application;

an [electrocardiogram] *electrocardiogragh* 1600 constructed to measure heart parameters;

a heart rate monitor 1620;

GPS hardware and machine instructions 1700;

a wireless transceiver 1800;

a speaker 1300 communicatively coupled to the wireless transceiver;

a battery 1900 that provides electrical energy to wireless transceiver 1800 and a processor 1920;

processor 1920 can be constructed to:

receive an electrical signal from battery 1900 and determine whether battery 1900 has a charge level that is above a predetermined threshold, wherein when the charge level is below the predetermined threshold, processor 1920 automatically suspends activities of processor 1920 after causing the wireless transceiver to transmit information comprising a location determined by GPS hardware and machine instructions 1700 and information concerning a user;

receive signals from [electrocardiogram] *electrocardiogragh* 1600 and/or heart rate monitor 1620;

determine, based upon [electrocardiogram] *electrocardiogragh* 1600 and/or heart rate monitor 1620 that an emergency has occurred, the emergency determined via creation of user heart norms and sets at least one alarm, the alarm based on one or more of:

a drop of a heartbeat frequency below a first threshold;

a spike of the heartbeat frequency above a second threshold; and a detected cessation in heart beat frequency; and without a user's touch, cause wireless transceiver 1800 to transmit information comprising the location determined by GPS hardware and machine instructions 1700 and information concerning the user.

a second touch screen 1220 constructed to render information concerning the emergency;

a biometric sensor 1240 that is constructed to identify the user based upon a unique characteristic of the user, wherein removal of the device is restricted unless the biometric sensor verifies identity of the user;

a microphone 1320 constructed to generate a signal responsive to human voices in proximity to the device, wherein the processor is constructed to recognize and interpret human speech to determine that the emergency has occurred; and a camera 1340 constructed to generate a signal responsive to motion in proximity to the device, wherein processor 1920 is constructed to recognize and interpret human actions from the signal from camera 1340 to determine that the emergency has occurred; and The determination that the emergency has occurred can be based upon a heart rate of the user being above a predetermined heart rate threshold. The determination that the emergency has occurred can be based upon the heart rate of the user being above a predetermined heart rate threshold.

The information comprising the location determined by the GPS hardware and machine instructions and information concerning the user is transmitted to an emergency medical system.

The device can send an alert if the GPS hardware and machine instructions determine that the device is located outside a predetermined location range. The device sends an alert if tampering with the device is detected. The device sends an alert if attempted removal of the device from the user is detected. The device sends an alert if attempted removal of the device from the user is detected after the charge level of the battery is below the predetermined threshold.

The device can send a response to a ping received by the wireless transceiver from an app, the ping requesting a location of the user based upon the GPS hardware and machine instructions.

Personal information concerning the user can be stored in a memory device comprised by the device, wherein signals transmitted from the device comprise the personal information.

Although device 1000 is illustrated as having a substantially annular shape, certain exemplary embodiments will comprise one or more portions that are flexible to allow device 1000 to conform more closely to a wrist of a user.

Certain exemplary embodiments that comprise [electrocardiogram] *electrocardiogragh* 1600 utilize one or more electrode type sensors that obtain information that is transmitted to processor 1920 and/or wireless transceiver 1800. In other embodiments, an external [electrocardiogram] *electrocardiogragh* can be utilized that transmits electrocardiogram information to device 1000 via wireless transceiver 1800.

Figure 2:
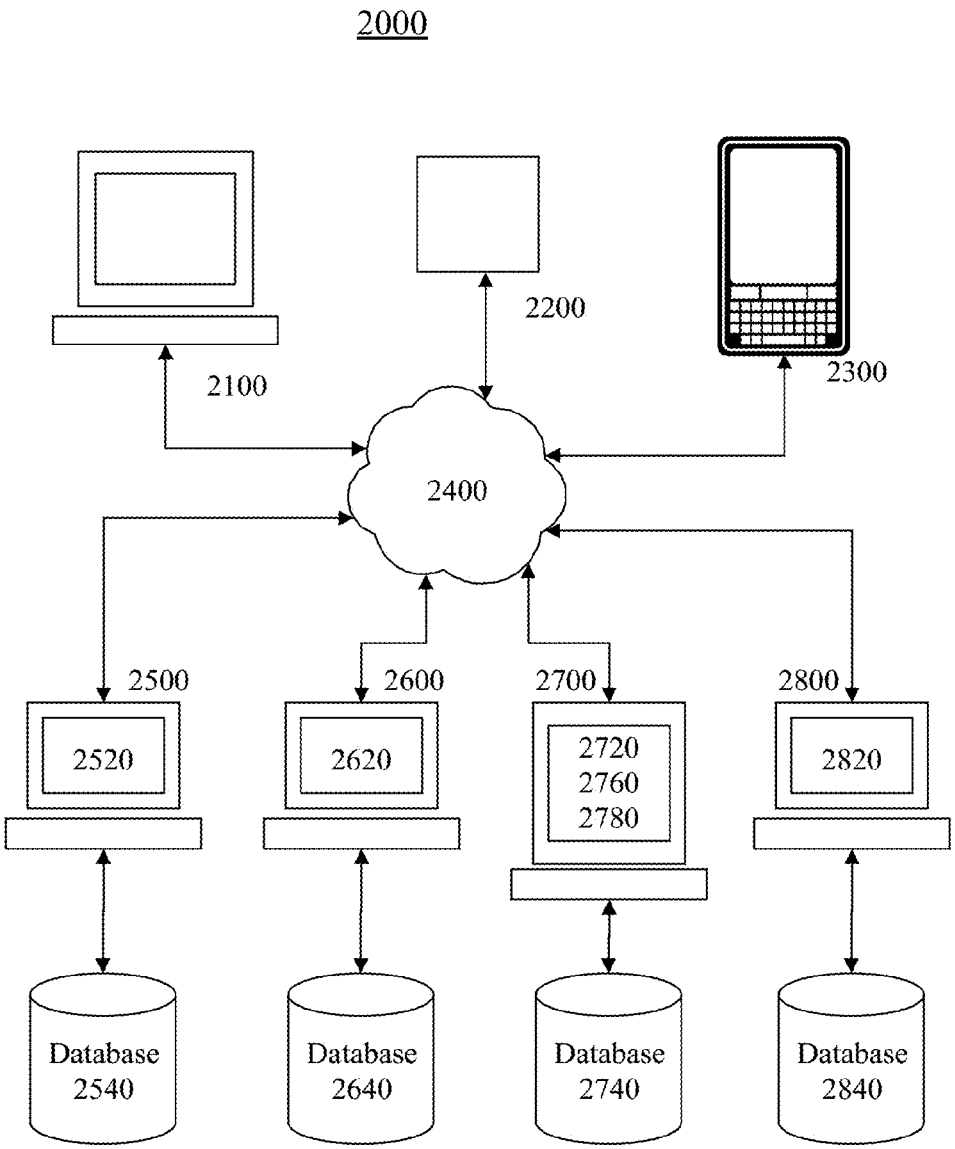
FIG. 2 is a block diagram of an exemplary embodiment of a system 2000.

FIG. 2 is a block diagram of an exemplary embodiment of a system 2000, which can comprise a smartphone 2300, an information device 2100, tablet 2200, a network 2400, a first server 2500, a second server 2600, a third server 2700, and a fourth server 2800. First server 2500 can comprise a first user interface 2520 and can be coupled to a first database 2540. Second server 2600 can comprise a second user interface 2620 and can be coupled to a second database 2640. Third server 2700 can comprise a third user interface 2720, a processor 2760, machine instructions 2780, and can be coupled to a third database 2740. Fourth server 2800 can comprise a fourth user interface 2820 and can be coupled to a fourth database 2840. Any of the methods and/or steps thereof can be carried out in whole or in part by tablet 2200, smartphone 2300, information device 2100 and/or first server 2500. Second server 2600, third server 2700, and/or fourth server 2800 can each be associated with implementation of a system via which rides are provided to customers. In certain exemplary embodiments, system 2000 can be used to implement one or more methods disclosed herein.

Figure 3:
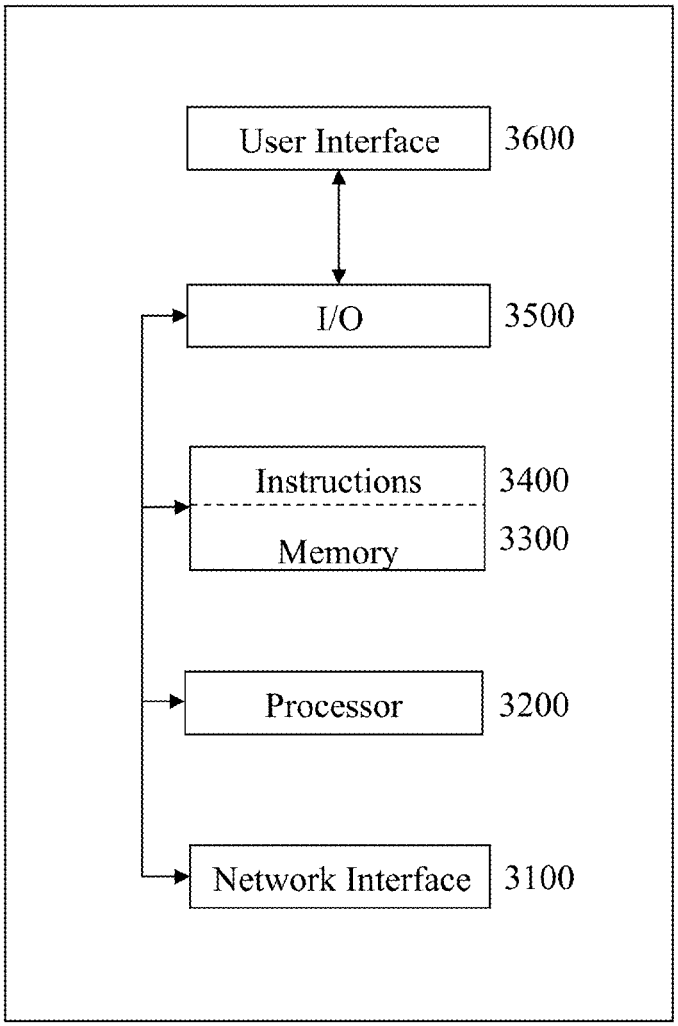
FIG. 3 is a block diagram of an exemplary embodiment of an information device 3000.

FIG. 3 is a block diagram of an exemplary embodiment of an information device 3000, which in certain operative embodiments can comprise, for example, first server 2500 and information device 2100, of FIG. 2. Information device 3000 can comprise any of numerous circuits and/or components, such as for example, one or more network interfaces 3100, one or more processors 3200, one or more memories 3300 containing instructions 3400, one or more input/output devices 3500, and/or one or more user interfaces 3600 coupled to one or more input/output devices 3500, etc.

In certain exemplary embodiments, via one or more user interfaces 3600, such as a graphical user interface, a user can view a rendering of information related to researching, designing, modeling, creating, developing, building, manufacturing, operating, maintaining, storing, marketing, selling, delivering, selecting, specifying, requesting, ordering, receiving, returning, rating, and/or recommending any of the products, services, methods, and/or information described herein.

Figure 4:
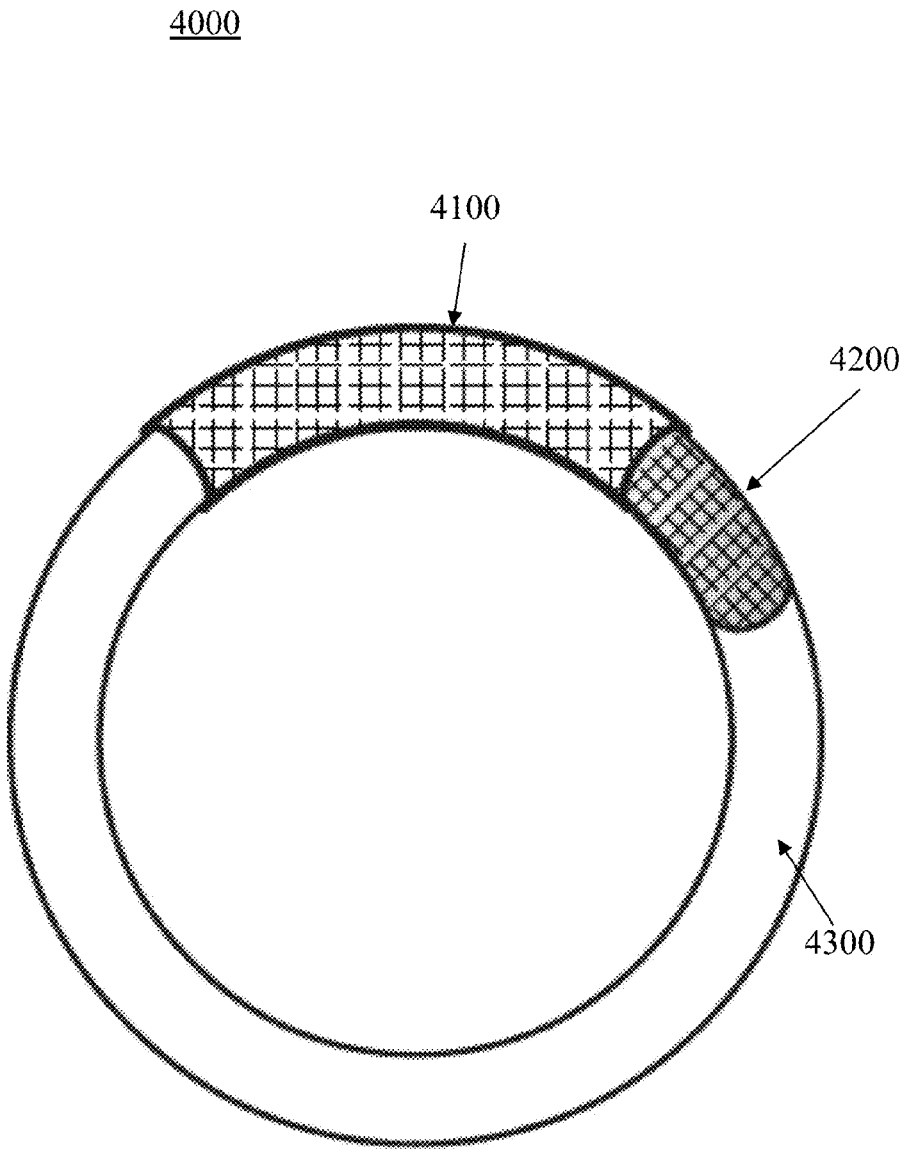
FIG. 4 is a perspective view of an exemplary embodiment of a device 4000.

FIG. 4 is a perspective view of an exemplary embodiment of a device 4000, which comprises a screen 4100, a speaker 4200, and a band 4300.

Figure 5:
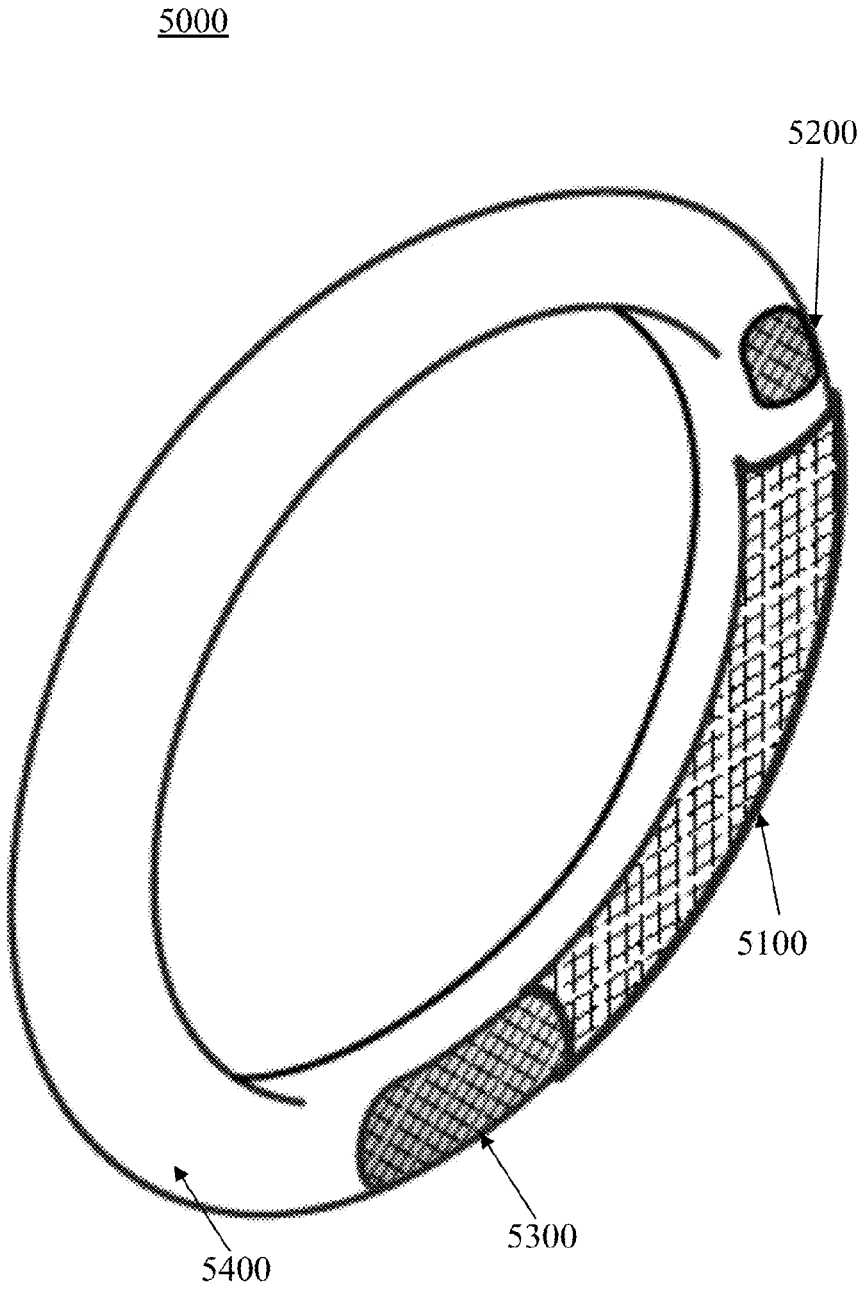
FIG. 5 is a perspective view of an exemplary embodiment of a device 5000.

FIG. 5 is a perspective view of an exemplary embodiment of a device 5000, which comprises a screen 5100, a speaker 5200, a microphone 5300, and a band 5400. Band 5400 can comprise a pull band portion.

Figure 6:
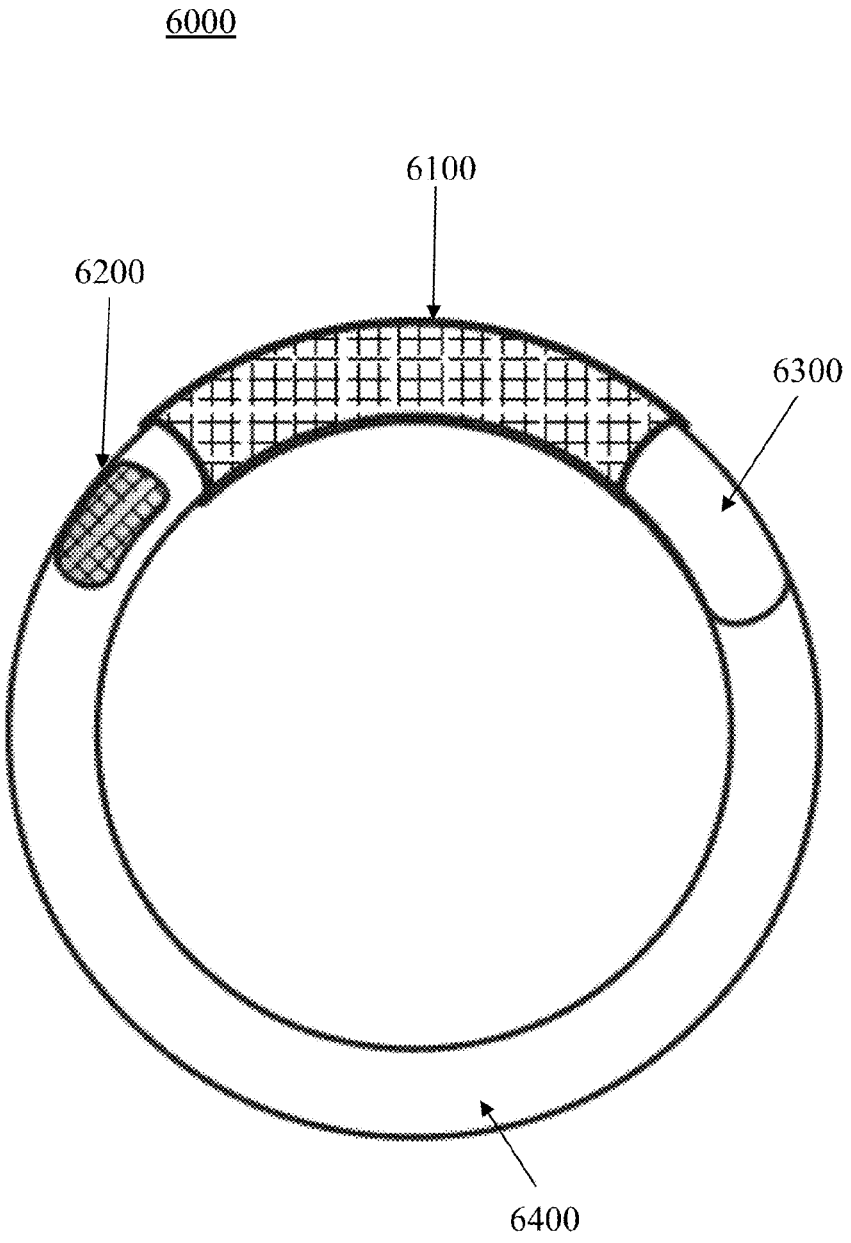
FIG. 6 is a perspective view of an exemplary embodiment of a device 6000.

FIG. 6 is a perspective view of an exemplary embodiment of a device 6000, which comprises a screen 6100, a speaker 6200, and a band 6300.

Figure 7:
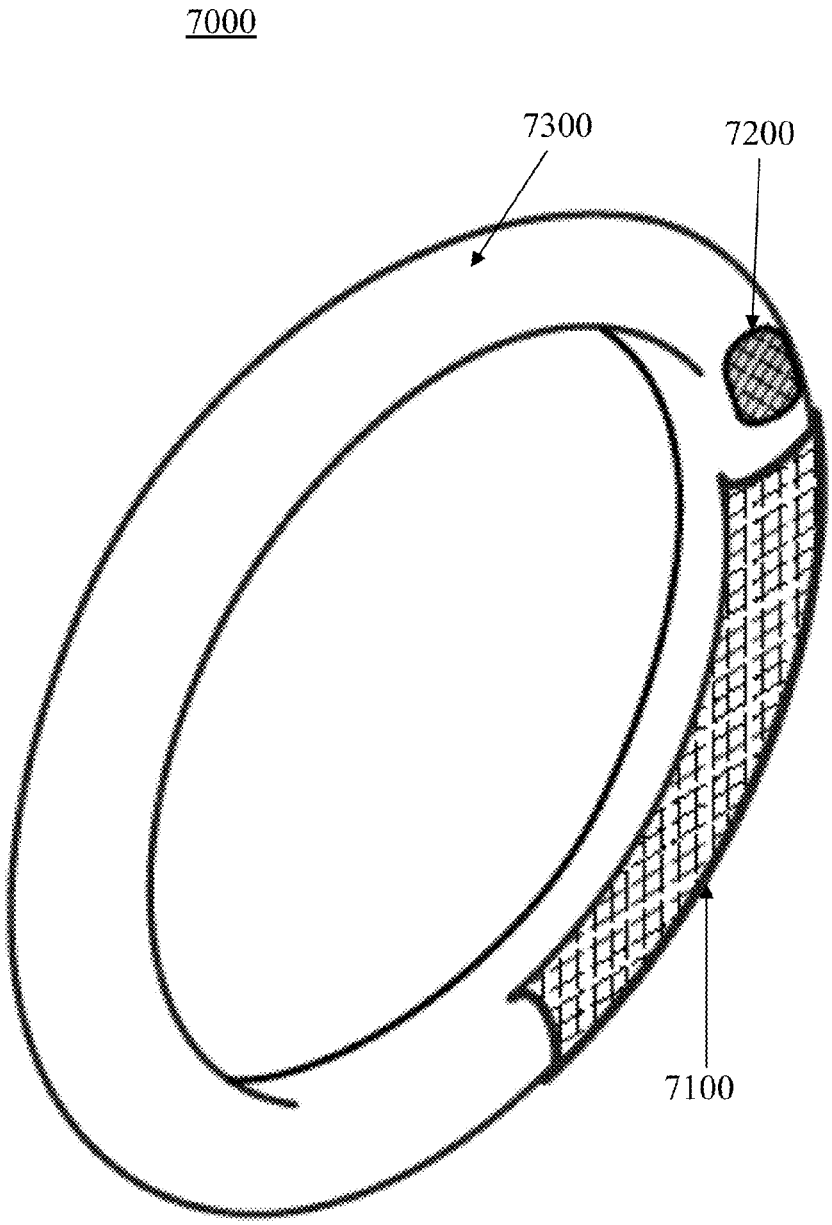
FIG. 7 is a perspective view of an exemplary embodiment of a device 7000.

FIG. 7 is a perspective view of an exemplary embodiment of a device 7000, which comprises a screen 7100, a speaker 7200, and a band 7300.

Figure 8:
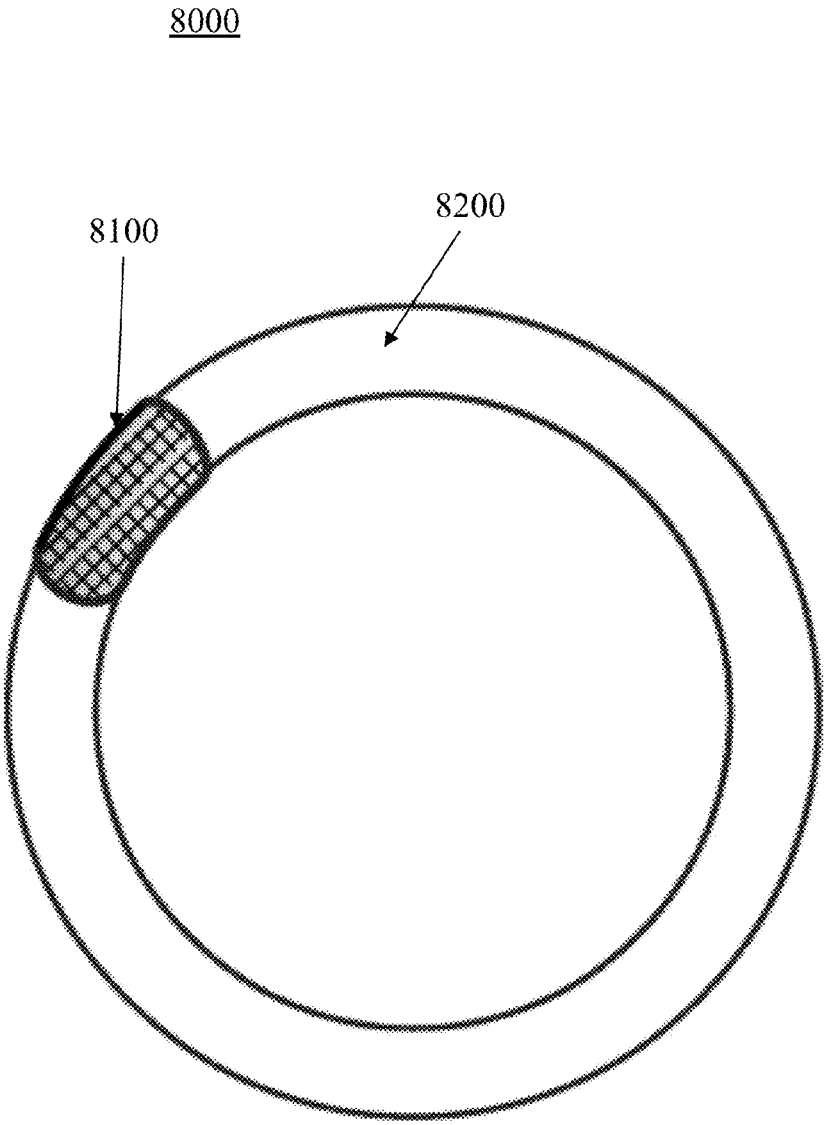
FIG. 8 is a perspective view of an exemplary embodiment of a device 8000.

FIG. 8 is a perspective view of an exemplary embodiment of a device 8000, which comprises a band 8200 and a speaker 8100.

Figure 9:
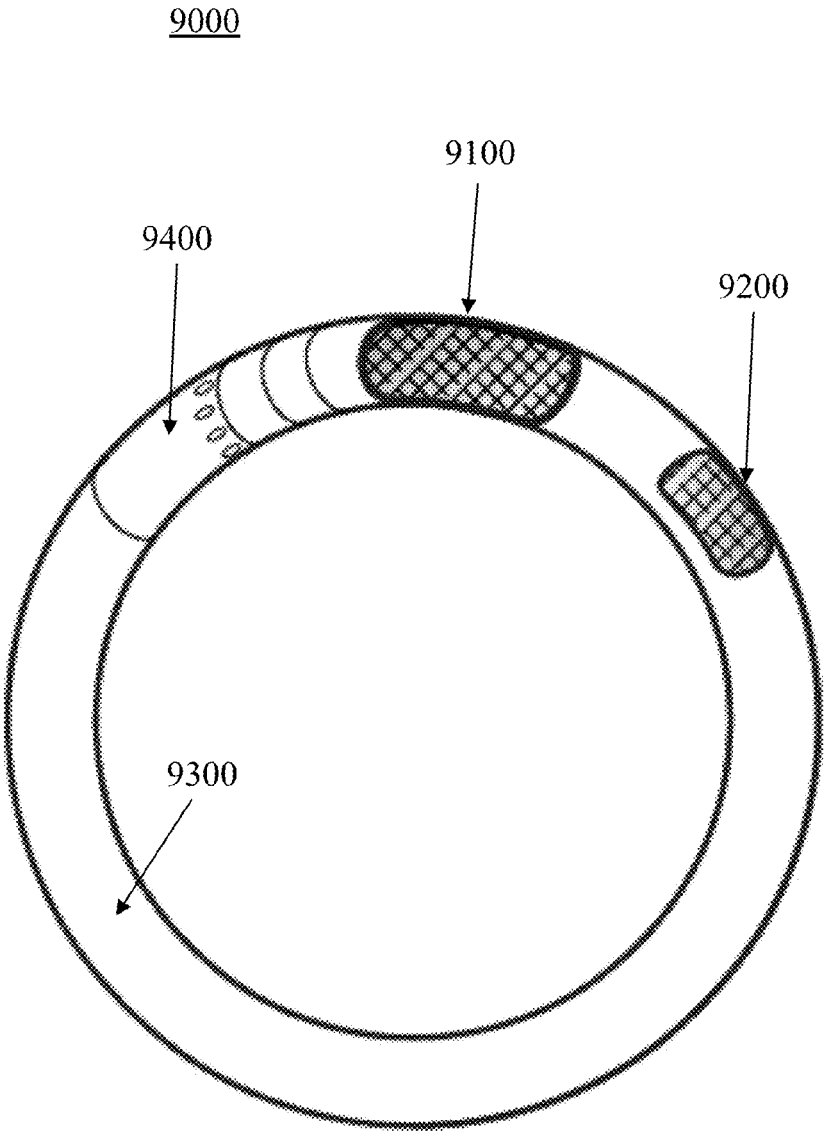
FIG. 9 is a perspective view of an exemplary embodiment of a device 9000.

FIG. 9 is a perspective view of an exemplary embodiment of a device 9000, which comprises a screen 9100, a speaker 9200, a band 9300, and a band adjustment 9400. Band adjustment 9400 can be used to adjust device 9000 to a wrist size of a wearer.

Definitions

When the following terms are used substantively herein, the accompanying definitions apply. These terms and definitions are presented without prejudice, and, consistent with the application, the right to redefine these terms during the prosecution of this application or any application claiming priority hereto is reserved. For the purpose of interpreting a claim of any patent that claims priority hereto, each definition (or redefined term if an original definition was amended during the prosecution of that patent), functions as a clear and unambiguous disavowal of the subject matter outside of that definition.

a—at least one.

activity—an action, act, step, and/or process or portion thereof.

adapter—a device used to effect operative compatibility between different parts of one or more pieces of an apparatus or system.

alarm—a warning of existing or approaching danger.

alert—an electrical, electronic, or mechanical device and/or display that serves to advise of a condition by means of a sound or signal.

and/or—either in conjunction with or in alternative to.

apparatus an appliance or device for a particular purpose.

arm—an upper human limb.

associate—to join, connect together, and/or relate.

attempt—to try to do something.

average population—a large number of people that in some sense are representative of a user.

automatically—acting or operating in a manner essentially independent of external influence or control. For example, an automatic light switch can turn on upon "seeing" a person in its view, without the person manually operating the light switch.

band—a circle of material.

baseline value—a standard magnitude of a parameter.

battery—one or more electrochemical cells adapted to convert stored chemical energy into electrical energy.

biometric—constructed to measure a physical characteristic.

biometric sensor—a sensor that provides a signal that can determine who a person is via one or more measured metrics of human physiology (e.g., fingerprint, palm veins, face recognition, DNA, palm print, hand geometry, iris recognition, retina, and/or scent, etc.).

brain wave—an electrical impulse in the brain.

camera—an instrument constructed to record and/or capture images.

can—is capable of, in at least some embodiments.

cause—to produce an effect.

cessation—stopage.

characteristic—a defining feature.

charge—to cause to store electrical energy such as in a battery.

charge level—an amount of electrical energy stored in a battery compared to a maximum level for a particular battery.

circuit—an electrically conductive pathway and/or a communications connection established across two or more switching devices comprised by a network and between corresponding end systems connected to, but not comprised by the network.

comprising—including but not limited to.

configure—to make suitable or fit for a specific use or situation.

connect—to join or fasten together.

constructed to—made to and/or designed to.

convert—to transform, adapt, and/or change.

couple—to linking in some manner.

create—to bring into being.

cut resistant—constructed to resist penetration of a blade and/or severance via the blade.

data—distinct pieces of information, usually formatted in a special or predetermined way and/or organized to express concepts.

decision tree—a tree algorithm in which the selection of each branch requires that some type of logical decision be made.

define—to establish the outline, form, or structure of.

demographical information—data concerning a section of a population sharing common characteristics, such as age, sex, class, etc.

detect—to sense or perceive.

determine—to obtain, calculate, decide, deduce, and/or ascertain.

device—a machine, manufacture, and/or collection thereof.

drop—to fall.

electrocardiogram—a recording of electrical activity of a human heart.

electroencephalogram—a non-invasive method to record electrical activity of the brain along a scalp; EEG measures voltage fluctuations resulting from ionic current flows within neurons of a brain emergency—a determined difference in measured physiological values that have been determined to have an important negative consequence in human physiology.

emergency medical system—a type of emergency service dedicated to providing medical care and/or transport to medical care.

energy—power derived from the utilization of physical or chemical resources.

estimate—to calculate and/or determine approximately and/or tentatively.

frequency—the number of times a specified periodic phenomenon occurs within a specified interval.

generate—to create, produce, give rise to, and/or bring into existence.

Global Positioning System ("GPS")—a system adaptable to determine a terrestrial location of a device receiving signals from multiple satellites.

glucometer—a medical device constructed to determine an approximate concentration of glucose in the blood.

group—a number of persons considered together as being related in some way.

haptic—involving the human sense of kinesthetic movement and/or the human sense of touch. Among the many potential haptic experiences are numerous sensations, body-positional differences in sensations, and time-based changes in sensations that are perceived at least partially in non-visual, non-audible, and non-olfactory manners, including the experiences of tactile touch (being touched), active touch, grasping, pressure, friction, traction, slip, stretch, force, torque, impact, puncture, vibration, motion, acceleration, jerk, pulse, orientation, limb position, gravity, texture, gap, recess, viscosity, pain, itch, moisture, temperature, thermal conductivity, and thermal capacity. —hardware—physical parts of an information device.

health parameters—a variable related to the physical well-being of a human.

heart norms—ranges of measureable values that are within predetermined values associated with good health.

heart rate monitor—a system constructed to measure a frequency of heartbeats.

hydrophobic coating—a substantially water-proof covering.

indication—a degree marked by an instrument.

identify—recognize a particular person or thing.

information device—any device capable of processing data and/or information, such as any general purpose and/or special purpose computer, such as a personal computer, workstation, server, minicomputer, mainframe, supercomputer, computer terminal, laptop, wearable computer, and/or Personal Digital Assistant (PDA), mobile terminal, Bluetooth device, communicator, "smart" phone (such as a Treo-like device), messaging service (e.g., Blackberry) receiver, pager, facsimile, cellular telephone, a traditional telephone, telephonic device, a programmed microprocessor or microcontroller and/or peripheral integrated circuit elements, an ASIC or other integrated circuit, a hardware electronic logic circuit such as a discrete element circuit, and/or a programmable logic device such as a PLD, PLA, FPGA, or PAL, or the like, etc. In general any device on which resides a finite state machine capable of implementing at least a portion of a method, structure, and/or or graphical user interface described herein may be used as an information device. An information device can comprise components such as one or more network interfaces, one or more processors, one or more memories containing instructions, and/or one or more input/output (I/O) devices, one or more user interfaces coupled to an I/O device, etc.

initialize—to prepare something for use and/or some future event.

input/output (I/O) device—any sensory-oriented input and/or output device, such as an audio, visual, haptic, olfactory, and/or taste-oriented device, including, for example, a monitor, display, projector, overhead display, keyboard, keypad, mouse, trackball, joystick, gamepad, wheel, touchpad, touch panel, pointing device, microphone, speaker, video camera, camera, scanner, printer, haptic device, vibrator, tactile simulator, and/or tactile pad, potentially including a port to which an I/O device can be attached or connected.

install—to connect or set in position and prepare for use.

interpret—to make sense of and/or assign a meaning to.

location—a place substantially approximating where something physically exists.

machine instructions—directions adapted to cause a machine, such as an information device, to perform one or more particular activities, operations, or functions. The directions, which can sometimes form an entity called a "processor", "kernel", "operating system", "program", "application", "utility", "subroutine", "script", "macro", "file", "project", "module", "library", "class", and/or "object", etc., can be embodied as machine code, source code, object code, compiled code, assembled code, interpretable code, and/or executable code, etc., in hardware, firmware, and/or software.

machine readable medium—a physical structure from which a machine can obtain data and/or information. Examples include a memory, punch cards, etc.

may—is allowed and/or permitted to, in at least some embodiments.

memory device—an apparatus capable of storing analog or digital information, such as instructions and/or data. Examples include a non-volatile memory, volatile memory, Random Access Memory, RAM, Read Only Memory, ROM, flash memory, magnetic media, a hard disk, a floppy disk, a magnetic tape, an optical media, an optical disk, a compact disk, a CD, a digital versatile disk, a DVD, and/or a raid array, etc. The memory device can be coupled to a processor and/or can store instructions adapted to be executed by processor, such as according to an embodiment disclosed herein.

method—a process, procedure, and/or collection of related activities for accomplishing something.

microphone—a device that converts sounds to an electrical signal.

motion—a process via which something changes position from one location to another.

network—a communicatively coupled plurality of nodes. A network can be and/or utilize any of a wide variety of sub-networks, such as a circuit switched, public-switched, packet switched, data, telephone, telecommunications, video distribution, cable, terrestrial, broadcast, satellite, broadband, corporate, global, national, regional, wide area, backbone, packet-switched TCP/IP, Fast Ethernet, Token Ring, public Internet, private, ATM, multi-domain, and/or multi-zone sub-network, one or more Internet service providers, and/or one or more information devices, such as a switch, router, and/or gateway not directly connected to a local area network, etc.

network interface—any device, system, or subsystem capable of coupling an information device to a network. For example, a network interface can be a telephone, cellular phone, cellular modem, telephone data modem, fax modem, wireless transceiver, Ethernet card, cable modem, digital subscriber line interface, bridge, hub, router, or other similar device.

occur—to take place.

Peak-Peak interval—an elapsed time between successive peaks of a signal.

personal information—data that is unique to a particular individual. For example, name, address, phone number, e-mail address, credit card number, and/or a photographic image, etc.

photoplethysmogram—an optically obtained volumetric measurement of an organ.

ping—to send a signal that requests a response.

plurality—the state of being plural and/or more than one.

population norm—a standard value for a large number of people.

predetermined—established in advance.

PR interval—the period, measured in milliseconds, that extends from the beginning of the P wave (the onset of atrial depolarization) until the beginning of the QRS complex (the onset of ventricular depolarization); it is normally between 120 and 200 ms in duration.

probability—a quantitative representation of a likelihood of an occurrence.

processor—a device and/or set of machine-readable instructions for performing one or more predetermined tasks. A processor can comprise any one or a combination of hardware, firmware, and/or software. A processor can utilize mechanical, pneumatic, hydraulic, electrical, magnetic, optical, informational, chemical, and/or biological principles, signals, and/or inputs to perform the task(s). In certain embodiments, a processor can act upon information by manipulating, analyzing, modifying, converting, transmitting the information for use by an executable procedure and/or an information device, and/or routing the information to an output device. A processor can function as a central processing unit, local controller, remote controller, parallel controller, and/or distributed controller, etc. Unless stated otherwise, the processor can be a general-purpose device, such as a microcontroller and/or a microprocessor, such the Pentium IV series of microprocessor manufactured by the Intel Corporation of Santa Clara, Calif. In certain embodiments, the processor can be dedicated purpose device, such as an Application Specific Integrated Circuit (ASIC) or a Field Programmable Gate Array (FPGA) that has been designed to implement in its hardware and/or firmware at least a part of an embodiment disclosed herein.

project—to calculate, estimate, or predict.

provide—to furnish, supply, give, and/or make available.

proximity—close to something.

pulse oximeter—an instrument constructed to measure oxygen saturation of hemoglobin in a sample of blood.

pulse wave—a kind of non-sinusoidal waveform that is similar to a square wave, but does not have a symmetrical shape associated with a perfect square wave.

P wave—an electrocardiogram pattern representing atrial depolarization, which results in atrial contraction.

QRS complex—the combination of three of the graphical deflections seen on an electrocardiogram.

QT interval—a measure of the time between the start of the Q wave and the end of the T wave in the heart's electrical cycle.

range—an area of effective operation.

receive—to get as a signal, take, acquire, and/or obtain.

recognize—to identify something.

recommend—to suggest, praise, commend, and/or endorse.

remove—to take something from a coupled location.

render—to make perceptible to a human, for example as data, commands, text, graphics, audio, video, animation, and/or hyperlinks, etc., such as via any visual, audio, and/or haptic means, such as via a display, monitor, electric paper, ocular implant, cochlear implant, speaker, etc.

repeatedly—again and again; repetitively.

request—to express a desire for and/or ask for.

resist—to be substantially unaltered from something and/or unharmed by something.

restrict—to limit one or more actions.

select—to make a choice or selection from alternatives.

set—a related plurality.

signal—information, such as machine instructions for activities and/or one or more letters, words, characters, symbols, signal flags, visual displays, and/or special sounds, etc. having prearranged meaning, encoded as automatically detectable variations in a physical variable, such as a pneumatic, hydraulic, acoustic, fluidic, mechanical, electrical, magnetic, optical, chemical, and/or biological variable, such as power, energy, pressure, flowrate, viscosity, density, torque, impact, force, frequency, phase, voltage, current, resistance, magnetomotive force, magnetic field intensity, magnetic field flux, magnetic flux density, reluctance, permeability, index of refraction, optical wavelength, polarization, reflectance, transmittance, phase shift, concentration, and/or temperature, etc. Depending on the context, a signal and/or the information encoded therein can be synchronous, asychronous, hard real-time, soft real-time, non-real time, continuously generated, continuously varying, analog, discretely generated, discretely varying, quantized, digital, broadcast, multicast, unicast, transmitted, conveyed, received, continuously measured, discretely measured, processed, encoded, encrypted, multiplexed, modulated, spread, de-spread, demodulated, detected, de-multiplexed, decrypted, and/or decoded, etc.

smart blood pressure sensor—a device and/or system that measures blood pressure via a plurality of sensors.

smart scale—a device and/or system constructed to weigh a person and to wirelessly transmit a signal indicative of the measured weight.

software applications (apps)—instructions constructed to operate a processor.

speaker—an electroacoustic device that emits sounds from an input signa, which sounds are audible to a human.

store—to place, hold, and/or retain data, typically in a memory.

ST segment depression—a value determined by measuring the vertical distance between the patient's trace and the isoelectric line at a location approximately 2-3 millimeters from the QRS complex.

ST segment elevation—an indicator of a myocardial infarction (i.e., heart attack) determined to have occurred via a measurement of a higher than normal connection between the QRS complex and the T wave in an electrocardiogram.

substantially—to a great extent or degree.

support—to bear the weight of, especially from below.

suspend—to stop something for a period of time.

system—a collection of mechanisms, devices, machines, articles of manufacture, processes, data, and/or instructions, the collection designed to perform one or more specific functions.

tamper—to meddle for the purpose of altering, damaging, or misusing.

threshold—a point that when exceeded produces a given effect or result.

touch—to contact something with a part of a human body.

touch screen—an input device and normally layered on the top of an electronic visual display of an information processing system. A user can give input or control the information processing system through simple or multi-touch gestures by touching the screen with a special stylus or one or more fingers.

transmit—to send as a signal, provide, furnish, and/or supply.

unauthorized—not permitted.

unique—specific to a particular individual.

utilize—to put to use.

user—any person, organization, process, device, program, protocol, and/or system that uses a device and/or service.

user interface—any device for rendering information to a user and/or requesting information from the user. A user interface includes at least one of textual, graphical, audio, video, animation, and/or haptic elements. A textual element can be provided, for example, by a printer, monitor, display, projector, etc. A graphical element can be provided, for example, via a monitor, display, projector, and/or visual indication device, such as a light, flag, beacon, etc. An audio element can be provided, for example, via a speaker, microphone, and/or other sound generating and/or receiving device. A video element or animation element can be provided, for example, via a monitor, display, projector, and/or other visual device. A haptic element can be provided, for example, via a very low frequency speaker, vibrator, tactile stimulator, tactile pad, simulator, keyboard, keypad, mouse, trackball, joystick, gamepad, wheel, touchpad, touch panel, pointing device, and/or other haptic device, etc. A user interface can include one or more textual elements such as, for example, one or more letters, number, symbols, etc. A user interface can include one or more graphical elements such as, for example, an image, photograph, drawing, icon, window, title bar, panel, sheet, tab, drawer, matrix, table, form, calendar, outline view, frame, dialog box, static text, text box, list, pick list, pop-up list, pull-down list, menu, tool bar, dock, check box, radio button, hyperlink, browser, button, control, palette, preview panel, color wheel, dial, slider, scroll bar, cursor, status bar, stepper, and/or progress indicator, etc. A textual and/or graphical element can be used for selecting, programming, adjusting, changing, specifying, etc. an appearance, background color, background style, border style, border thickness, foreground color, font, font style, font size, alignment, line spacing, indent, maximum data length, validation, query, cursor type, pointer type, autosizing, position, and/or dimension, etc. A user interface can include one or more audio elements such as, for example, a volume control, pitch control, speed control, voice selector, and/or one or more elements for controlling audio play, speed, pause, fast forward, reverse, etc. A user interface can include one or more video elements such as, for example, elements controlling video play, speed, pause, fast forward, reverse, zoom-in, zoom-out, rotate, and/or tilt, etc. A user interface can include one or more animation elements such as, for example, elements controlling animation play, pause, fast forward, reverse, zoom-in, zoom-out, rotate, tilt, color, intensity, speed, frequency, appearance, etc. A user interface can include one or more haptic elements such as, for example, elements utilizing tactile stimulus, force, pressure, vibration, motion, displacement, temperature, etc.

verify—to confirm.

via—by way of and/or utilizing.

warning—information that alerts someone of a potentially harmful condition.

weight—a value indicative of importance.

wireless transceiver—a device constructed to transfer signals between sources and destinations without the use of wires.

Note

Still other substantially and specifically practical and useful embodiments will become readily apparent to those skilled in this art from reading the above-recited and/or herein-included detailed description and/or drawings of certain exemplary embodiments. It should be understood that numerous variations, modifications, and additional embodiments are possible, and accordingly, all such variations, modifications, and embodiments are to be regarded as being within the scope of this application.

Thus, regardless of the content of any portion (e.g., title, field, background, summary, description, abstract, drawing figure, etc.) of this application, unless clearly specified to the contrary, such as via explicit definition, assertion, or argument, with respect to any claim, whether of this application and/or any claim of any application claiming priority hereto, and whether originally presented or otherwise:

- there is no requirement for the inclusion of any particular described or illustrated characteristic, function, activity, or element, any particular sequence of activities, or any particular interrelationship of elements;
- no characteristic, function, activity, or element is "essential";
- any elements can be integrated, segregated, and/or duplicated;
- any activity can be repeated, any activity can be performed by multiple entities, and/or any activity can be performed in multiple jurisdictions; and
- any activity or element can be specifically excluded, the sequence of activities can vary, and/or the interrelationship of elements can vary.

Moreover, when any number or range is described herein, unless clearly stated otherwise, that number or range is approximate. When any range is described herein, unless clearly stated otherwise, that range includes all values therein and all subranges therein. For example, if a range of 1 to 10 is described, that range includes all values therebetween, such as for example, 1.1, 2.5, 3.335, 5, 6.179, 8.9999, etc., and includes all subranges therebetween, such as for example, 1 to 3.65, 2.8 to 8.14, 1.93 to 9, etc.

When any claim element is followed by a drawing element number, that drawing element number is exemplary and non-limiting on claim scope. No claim of this application is intended to invoke paragraph six of 35 USC 112 unless the precise phrase "means for" is followed by a gerund.

Any information in any material (e.g., a United States patent, United States patent application, book, article, etc.)

that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such material is specifically not incorporated by reference herein.

Accordingly, every portion (e.g., title, field, background, summary, description, abstract, drawing figure, etc.) of this application, other than the claims themselves, is to be regarded as illustrative in nature, and not as restrictive, and the scope of subject matter protected by any patent that issues based on this application is defined only by the claims of that patent.

What is claimed is:

1. A device comprising:

an [electrocardiogram] *electrocardiograph* constructed to measure heart parameters;

GPS hardware and machine instructions;

a wireless transceiver;

a processor constructed to:

receive an electrical signal from a battery and [determines] *determine* whether the battery has a charge level that is above a predetermined threshold, wherein when the charge level is below the predetermined threshold, the processor automatically suspends activities of the processor after causing the wireless transceiver to transmit information comprising a location determined by the GPS hardware and machine instructions and information concerning a user;

receive signals from the [electrocardiogram] *electrocardiograph*;

determine, based upon the *signals from the* [electrocardiogram] *electrocardiograph* that an emergency has occurred, the emergency determined via creation of user heart norms and [sets] *setting* at least one alarm, the alarm based on one or more of:

a drop of a heartbeat frequency below a first threshold;

a spike of the heartbeat frequency above a second threshold; and a detected cessation in [heart beat] *heartbeat* frequency; and without a touch of the user, cause the wireless transceiver to transmit the information comprising the location determined by the GPS hardware and machine instructions and the information concerning the user;

*wherein* the battery [that] provides electrical energy to the wireless transceiver and the processor; and a band comprising a cut resistant material, the cut resistant material constructed to resist unauthorized removal of the band from an arm of the user.

2. The device of claim 1, further comprising:

a touch screen constructed to utilize a software application.

3. The device of claim 1, further comprising:

a first touch screen constructed to utilize a software application; and a second touch screen constructed to render information concerning the emergency.

4. The device of claim 1, further comprising:

a speaker communicatively coupled to the wireless transceiver.

5. The device of claim 1, further comprising:

a biometric sensor that is constructed to identify the user based upon a unique characteristic of the user, wherein removal of the device is restricted unless the biometric sensor verifies identity of the user.

6. The device of claim 1, further comprising:

a microphone constructed to generate a signal responsive to human voices in proximity to the device, wherein the processor is constructed to recognize and interpret human speech to determine that the emergency has occurred; and without the touch of the user, cause the wireless transceiver to transmit the information comprising the location determined by the GPS hardware and machine instructions and the information concerning the user.

7. The device of claim 1, further comprising:

a camera constructed to generate a signal responsive to motion in proximity to the device, wherein the processor is constructed to recognize and interpret human actions from the signal from the camera to determine that the emergency has occurred; and without the touch of the user, cause the wireless transceiver to transmit the information comprising the location determined by the GPS hardware and machine instructions and the information concerning the user.

[8. The device of claim 1, wherein the determination that the emergency has occurred is based upon a heart rate of the user being above a predetermined heart rate threshold.]

[9. The device of claim 1, wherein the determination that the emergency has occurred is based upon a heart rate of the user being above a predetermined heart rate threshold.]

10. The device of claim 1, wherein the information comprising the location determined by the GPS hardware and machine instructions and the information concerning the user is transmitted to an emergency medical system.

11. The device of claim 1, wherein the device sends an alert if the GPS hardware and machine instructions determine that the device is located outside a predetermined location range.

12. The device of claim 1, wherein the device sends an alert if tampering with the device is detected.

13. The device of claim 1, wherein the device sends an alert if attempted removal of the device from the user is detected.

14. The device of claim 1, wherein the device sends an alert if attempted removal of the device from the user is detected after the charge level of the battery is below the predetermined threshold.

15. The device of claim 1, wherein the device sends a response to a ping received by the wireless transceiver from an app, the ping requesting a location of the user based upon the GPS hardware and machine instructions.

16. The device of claim 1, wherein personal information concerning the user is stored in a memory device comprised by the device, wherein signals transmitted from the device comprise the personal information.

17. A device comprising:

a heart rate monitor constructed to measure heartbeat frequency;

GPS hardware and machine instructions;

a wireless transceiver;

a processor constructed to:

receive an electrical signal from a battery and [determines] *determine* whether the battery has a charge level that is above a predetermined threshold, wherein when the charge level is below the predetermined threshold, the processor automatically suspends activities of the processor after causing the wireless transceiver to transmit information comprising a location determined by the GPS hardware and machine instructions and information concerning a user;

receive signals from the heart rate monitor;

determine, based upon the heart rate monitor that an emergency has occurred; and without a touch of the user, cause the wireless transceiver to transmit the information comprising the location determined by the GPS hardware and machine instructions and the information concerning the user;

*wherein* the battery [that] provides electrical energy to the wireless transceiver and the processor; and a band comprising a cut resistant material, the cut resistant material constructed to resist unauthorized removal of the band from an arm of the user.

*18. A method of transmitting information concerning a wearer during an emergency, the method comprising:*

*providing a heart rate monitor configured to measure heartbeat frequency of a wearer, a global positioning sensor, a wireless transceiver, a processor, and a battery all operatively coupled into a band comprising a cut resistant material, the band configured to be worn by the wearer;*

*receiving an electrical signal from the battery;*

*determining whether the battery has a charge level that is above a predetermined threshold, wherein when the charge level is below the predetermined threshold, automatically suspending activity of the processor after transmitting, using the wireless transceiver, information comprising a location of the wearer determined by the global positioning sensor;*

*determining, based upon the heartbeat frequency of the wearer measured by the heart rate monitor that an emergency has occurred; and*

*without a touch of the wearer, transmitting, using the wireless transceiver, information comprising a location of the wearer determined by the global positioning sensor.*

*19. The method of claim 18, wherein determining that an emergency has occurred further comprises:*

*creating wearer heart norms using the processor and the heart rate monitor; and establishing at least one alarm using the processor.*

*20. The method of claim 19, wherein establishing at least one alarm further comprises one or more of:*

*detecting a drop of the heartbeat frequency of the wearer below a first threshold;*

*detecting a spike of the heartbeat frequency above a second threshold; or*

*detecting a cessation of the heartbeat frequency.*

*21. The method of claim 18, further comprising sending an alert if the global positioning sensor and processor determine the band is outside a predetermined location range.*

*22. The method of claim 18, further comprising sending an alert if attempted removal of the band from the wearer is detected by the processor.*

* * * * *